(12) United States Patent
Bevan et al.

(10) Patent No.: US 7,871,968 B2
(45) Date of Patent: Jan. 18, 2011

(54) MEDICINAL SOAP COMPRISING SAPROPEL

(75) Inventors: Rupert Bevan, Radstock (GB); Michael John Smith, Bath (GB)

(73) Assignee: Saponaqua International Limited, London (GB)

( * ) Notice: Subject to any disclaimer, the term of this patent is extended or adjusted under 35 U.S.C. 154(b) by 335 days.

(21) Appl. No.: 10/597,440

(22) PCT Filed: Jan. 21, 2005

(86) PCT No.: PCT/GB2005/000226

§ 371 (c)(1),
(2), (4) Date: Apr. 12, 2007

(87) PCT Pub. No.: WO2005/070385

PCT Pub. Date: Aug. 4, 2005

(65) Prior Publication Data

US 2007/0173424 A1 Jul. 26, 2007

(30) Foreign Application Priority Data

Jan. 26, 2004 (GB) .................................. 0401634.1

(51) Int. Cl.
*A61K 7/00* (2006.01)
(52) U.S. Cl. .................. 510/130; 510/159; 510/481; 510/491; 510/458; 510/462; 424/70.1

(58) Field of Classification Search ....................... None
See application file for complete search history.

(56) References Cited

U.S. PATENT DOCUMENTS

| 3,772,191 | A | 11/1973 | Thorn |
| 6,267,962 | B1 | 7/2001 | Hart et al. |
| 2005/0112084 | A1* | 5/2005 | O'Grady et al. ................ 424/73 |
| 2006/0121807 | A1* | 6/2006 | Albrecht et al. .............. 442/121 |
| 2008/0251462 | A1 | 10/2008 | Bevan |

FOREIGN PATENT DOCUMENTS

| GB | 451559 | | 8/1936 |
| GB | 2200351 | | 8/1988 |
| RO | 64548 | | 10/1978 |
| RO | 79211 | | 6/1982 |
| RU | 2091538 | | 9/1997 |
| RU | 2124397 | | 1/1999 |
| RU | 2180213 | * | 7/2000 |
| RU | 2170094 | | 7/2001 |
| RU | 2185814 | * | 7/2001 |
| RU | 2180213 | | 3/2002 |
| RU | 2197224 | | 1/2003 |

* cited by examiner

*Primary Examiner*—Necholus Ogden, Jr.
(74) *Attorney, Agent, or Firm*—Pabst Patent Group LLP

(57) ABSTRACT

The present invention provides soap, including glycerine and sapropel. It also provides therapeutic uses thereof.

8 Claims, No Drawings

MEDICINAL SOAP COMPRISING SAPROPEL

This application is a National Stage of International Application No. PCT/GB2005/000226 filed on Jan. 21, 2005, which claims priority to GB Application No. 0401634.2 filed on Jan. 26, 2004.

The present invention relates to a surfactant. More particularly, the present invention relates to a surfactant used for cleaning. More particularly, the present invention relates to soap. In one embodiment, the present invention relates to a medicinal soap that alleviates and/or arrests the symptoms brought about by, or associated with, diseases and/or conditions such as eczema, dermatitis, acne, psoriasis, athlete's foot and various skin allergies.

Soap is an anionic surfactant. Soaps are made from fats and oils, or their fatty acids, by treating them chemically with a strong alkali. The fats and oils used in making soap generally come from animal or plant sources. Each fat or oil is made up of distinctive mixture of several triglycerides, each triglyceride including three fatty acid molecules attached to one molecule of glycerine. There are many different types of triglycerides; each type consisting of its own particular combination of fatty acids.

Saponification of fats and oils is the most commonly used soap making process. This involves heating the fats and oils, and reacting them with an alkali, usually in liquid form, to produce soap and water (neat soap) and glycerine.

Another process for making soap involves the neutralisation of fatty acids with an alkali. In this process, the fats and oils are hydrolysed with a high pressure steam to yield crude fatty acids and glycerine. The fatty acids are then purified by distillation and subsequently neutralised with an alkali to produce soap and water (neat soap).

One of the by-products of the soap making process is glycerine. Glycerine is usually removed from the final product, because it is inclined to soften the soap and moreover, due to its inherent moisturising qualities is perceived to have greater value as a base for shampoos, bath oils, skin creams and like products.

When the alkali is sodium hydroxide, a sodium soap is formed. Sodium soaps are "hard/solid" soaps. When the alkali is potassium hydroxide, a potassium soap is formed. Potassium soaps are softer and are found in some liquid hand soaps and shaving creams. Contextually, it is to be understood that any reference to a sodium soap is to be construed to mean that the soap product is hard or in solid form, for example, a bar of soap of any shape, and that any reference to a potassium soap is to be construed to mean that the soap product is in liquid or gel form, for example, a liquid hand soap.

Some soaps tend to absorb moisture from the skin leaving the skin dry. This can exacerbate certain skin conditions caused by dry skin, for example, eczema. In addition, it is not uncommon for certain constituents of soap, for example, colourants etc. added to the soap to make it more desirable to act as an allergen. As a result, there is a need to provide soaps, which are moisturising and/or hypoallergenic.

Sapropel is a clay-like material, which is known as a source material for oil and natural gas. The term, sapropel, is derived from the Greek sapros, meaning "decayed" and pelos meaning "mud", and denotes a range of marine and lacustrine sediments containing organic and inorganic components. Sapropels range from the black organic oozes associated with the Silurian rock formations to variously coloured Holocene deposits.

Tabulated below is a list of countries and regions of the world where sapropel is reported to be found, together with a description of geological age.

TABLE 1

Table 1: Countries and regions of the world where sapropel is reported to be found, together with description of geological age. Source: Andersons (1996).

| Continent | Type of deposit |
|---|---|
| Northern Europe: | |
| Finland | Lacustrine Quaternary |
| Sweden | " |
| Estonia | " |
| Larvia | " |
| Lithuania | " |
| Denmark | " |
| Netherlands | " |
| Baltic Sea | Marine Quaternary |
| Central Europe: | |
| Czech Republic | Lacustrune Quarternary |
| East Germany | " |
| Poland | " |
| Northern Italy | " |
| Romania | " |
| Southern Europe: | |
| Mediterranean Sea | Marine Silurian - Quarternary |
| Black Sea region | " |
| CIS: | |
| Belarus | Lacustrine Quaternary |
| Ukraine | " |
| Russia | " |
| Kaleria | " |
| Siberia: Omsk | " |
| Yakutsk | " |
| Nizhny Novgorod | " |
| Tomsk | " |
| The USA: | |
| Arkansas | Lacustrine Quaternary |
| Florida | " |
| Minnesota | " |
| Nebraska | " |
| Wisconsin | " |
| Canada | Lacustrine Quaternary |
| South America: | |
| Venezuelan coast | Marine Quarternary |
| Australia: | |
| Lake Cooroong | Lacustrine Quarternary |
| Africa: | |
| Namibia | Lacustrine Quaternary |

Deposits of sapropel are mainly associated with sub-boreal lakes of Northern Europe, Siberia, Canada and the northern states of the U.S.A. Within Europe there are concentrations of sapropel-rich lakes in Karelia, Estonia, Latvia, Lithuania, Poland and the Czech Republic. Smaller amounts are reported to exist in Denmark, Finland, Sweden, the Netherlands, northern Italy and eastern parts of Germany. Extensive deposits are also found in the Russian Federation, Belarus and Ukraine.

As will be appreciated, not all sapropels are found as lake deposits. They may have their origin in peat formed in subsequent layers of vegetation. For example, sapropel from the Lake Sakhtysh region of north-west Russia is mined from beneath dry peat land.

Marine sapropels can also occur which are also Holocene. They are associated with the seas bordering arid regions, such as Namibia and the Sierra Nevada of Venezuela, and the eastern Mediterranean and Black Sea in Europe.

In the European regions, sapropels have been reported to form at a rate of 1 mm per annum. The organic components of sapropel accumulates in micro-laminations from a continuous rain of organic debris originating in vast reed beds bordering the lakes and is therefore autochthonous, i.e. originating from within the area of the lake. The inorganic component of sapropel is probably allochthonous, i.e. originating from outside the lake, but the migration of certain minerals such as calcium, magnesium and sulphur may originate from allochthonous organic sources.

Many sapropels are almost white-to-cream coloured. This reflects the amount of organic matter contained therein. As will be appreciated, as the organic component within the sapropel increased it will assume a darker colour; some sapropels are jet black.

Sapropels exhibit varying alkalinity. In this connection, sapropels having a pH greater than 7 are termed "lime-sapropels" and are usually characterised by the presence of several species of snails.

Sapropel can form in marine environments, as well as in freshwater lakes.

In marine environments, where the sea floor is too deep to allow oxygen to remain dissolved, sulphur-rich water acts as a reducing agent and provides an environment where organic debris can form sapropel. The sulphur itself is derived from the partial decomposition of plant and animal matter. In the areas of the sea beds where deposits of sapropel are found, the adjacent landmass is usually arid and well-leached of plant-growth supporting minerals. This may result in a correspondingly high supply of nutrients supporting a rich diversity of biota off the coast.

Typically, sapropel-rich lakes are situated on low-lying land. Generally, the lake bedrock is relatively insoluble and the lakeside soils tend to be podzols, from which nutrients are easily leached. As will be appreciated, the lakes themselves become sumps for these mobilised mineral salts, which are assimilated by reed beds that act as water-purifying agents. Sapropel forms on the lake floor in much the same way as peat forms on a raised or blanket bog. The organic compound is derived from limnic (surface) vegetation, in particular, reeds. As these herbaceous plants pass through their annual cycle of growth and decay, they give rise to a continuous stream of organic waste material that accumulates on the lakebed. Here decomposition is continued in the form of digestion of the lignified tissues. Sulphur from protein bonding is liberated in the form of hydrogen sulphide gas, which combines with dissolved oxygen to form soluble sulphurous acid. In a typical sapropel lake, there is little replacement oxygen as the water tends to be stagnant, and after a while, all the available oxygen is used up such that decomposition slow down, and eventually stops altogether. Thereafter, the digestion of organic material becomes anaerobically controlled, giving rise to chemical reductions and the precipitation of certain minerals.

Some lakes have been accumulating sapropel undisturbed for over 10,000 years. In some places, deposits of sapropel have displaced nearly all of the water. For example, Lake Zebris in Latvia has approximately a half meter depth of water remaining.

As will be appreciated not all sapropel deposits are found in the lacustrine environment. For example, in the Lake Sakhtysh region of northern Russia, water has receded in recent time and some of the former lake land has undergone a succession to moss or reed beds, with a layer of peat formed above the sapropel deposit.

In the past, sapropel has been utilised as a fertiliser. In this connection, the use of sapropel as a fertiliser has not been pursued due to its low nitrogen content; this, despite the fact, that many attempts have been made to increase its nitrogen content. In addition; due to its mineral content, sapropel has also been utilised in some courtiers as a supplement to animal feed.

In a first aspect of the present invention there is provided soap characterised in that the soap includes sapropel and glycerine.

Based on their research, the inventors have surprisingly discovered that there is a synergy between glycerine, which is usually removed from soap, and sapropel when present in soap. Such synergy resulting in a soap which is not only moisturising, but also arrests or reverses the symptoms, for example, cracked skin, associated with, or brought about by, skin complaints, diseases or conditions such as eczema, dermatitis, psoriasis, acne, athlete's foot and skin allergies.

In a further aspect of the present invention there is provided the soap of the present invention for use as a medicament. In particular, the soap of the present invention can be used to arrest or reverse the symptoms of cracked skin and/or itchiness and/or weeping and/or rashes indicative of skin complaints or conditions such as eczema, dermatitis, psoriasis, acne, athletes foot and skin allergies.

In addition, another advantage of including sapropel is that being mildly abrasive it has the added advantage of acting as an exfoliant.

A process for making three non-limiting embodiments of soap in accordance with the present invention will now be described by way of reference to Table 1 below, which lists the reactants utilised to make three different types of soap of the present invention. Such soaps internally designated 1398, 1397 and 1393 respectively.

TABLE 1

| | | | Oil | | | | | | |
|---|---|---|---|---|---|---|---|---|---|
| | Olive Oil % | Coconut Oil % | Castor Oil % | Beeswax % | Fragrance g Colour | Rainwater g | NaOH g | Sapropel Dry white g | Sapropel Dry black g |
| Function | Main ingredient | Lathering agent | Hardener | Catalyses saponification | Appeal | | | | |
| Soap 1398 Bay Rum 100 × 80 g bars approx Oil mass: 8332 g (5% superfatted*) | 48 | 42 | 8 | 2 | Bay Rum 60 Rosewood 30 Orange 20 Pine 10 Turmeric 20 | 3165 | 1297 | 10 | |

TABLE 1-continued

| | Olive Oil % | Coconut Oil % | Castor Oil % | Beeswax % | Fragrance g Colour | Rainwater g | NaOH g | Sapropel Dry white g | Sapropel Dry black g |
|---|---|---|---|---|---|---|---|---|---|
| Soap 1397 Pelo Two Oil mass: 8334 g (5% superfatted*) | 66 | 30 | 2 | 2 | Orange 60 Bergamot 30 Bay Rum 20 Pine 5 Turmeric 20 | 3165 | 1245 | 10 | |
| Soap 1393 Pelo Hortus (5% superfatted*) | 50 | 40 | 5 | 5 | Pine 50 Litsia 10 Bergamot 10 Chlorophyll 20 | 3040 | 1222 | | 160 |

*superfatted = % of surplus of oils over that usually required to achieve saponification The sapropel component of the soap was first prepared. In the event that the sapropel component was black sapropel, it was oven dried by convection and then dry roasted to arrive at a fine powder. In the event that the sapropel component was white sapropel, it was air dried and subsequently ground to form a fine powder.

The beeswax, which was included to catalyse the saponification reaction resulting in the soap, was then heated until it was in liquid form. So too were the coconut oil and the olive oil. Both were heated to approximately 65° C. and then, with a view to facilitating the blending of the oils, were cooled to 40° C.

The NaOH was then added to the water and was allowed to stand until it had reached the same temperature as the oils, approximately 40° C.

The oils and mixture of water an NaOH were then added to a batch reactor, preferably a steam double boiler with offset rotary paddle. In addition, in order to catalyse the reaction, soap from a previous batch was also added to the reactant mixture.

After about an hour, the pH of the reactant mixture was tested. When a pH of about 8 had been reached the desired fragrances and colour constituents were added.

The resultant mixture, whilst still in a liquid state, was subsequently poured off into stainless steel column moulds, insulated and placed in a warm room where they remained for 6 days. This enabled the saponification reaction to continue in the moulds until the mixture solidifies.

The resultant soap was then removed from the moulds and allowed to dry for a further 2 weeks. The soap was then subsequently cut into bars and stacked for 8 weeks, during which time the soap loses water, shrinks and stabilises.

As regards the tests conducted with a view to confirming the efficacy of the soap of the present invention as a medicament, which can arrest and/or reverse symptoms such as cracked skin and/or itchiness and/or weeping and/or rashes associated with skin complaints and diseases such as eczema, dermatitis, acne, psoriasis, athlete's foot and allergies; the following investigations were conducted.

A test group of approximately 30 people of mixed gender and varying age all suffering from at least one of the above skin conditions were selected.

Each member of the group was told to discontinue any previous medications they may have been using at the time to arrest or treat the symptoms associated with the skin condition/disease from which they suffered, and moreover, were instructed to wash the affected area of their body with warm water and the soap of the present invention at least twice daily.

Tabulated below are some of the results of our investigations:

| Gender | Age | Condition | Symptoms | Observations |
|---|---|---|---|---|
| Male | 43 | Psoriasis | Patches of itchy, scaly skin | Symptoms alleviated within 10 days of starting treatment |
| Female | 51 | Psoriasis | Patches of itchy, scaly skin | Symptoms alleviated within 3 days of starting treatment |
| Female | 45 | Psoriasis | Patches of itchy, scaly skin | Symptoms alleviated within 4 days of starting treatment |
| Female | 5 | Eczema | Dry, itchy patches of skin | Symptoms almost eradicated after 7 days of starting treatment |
| Female | 25 | Eczema | Areas of dry, itchy skin particularly around the eyebrows, hairline and between fingers | Symptoms almost eradicated overnight |
| Female | 25 | Daffodil Allergy | Red, puffy, itchy areas of skin on arms | Symptoms eradicated almost overnight after starting treatment |
| Male | 4 | Eczema | Itchy, scratchy, weeping eyes | Symptoms eradicated by daily washing after approximately 3 days |
| Male | 44 | Athletes Foot | Itchy, cracked skin between toes | Symptoms eradicated within 3 days of starting treatment |
| Male | 50 | Athletes Foot | Itchy, cracked skin between toes | Symptoms eradicated within 4 days of starting treatment |
| Male | 18 | Acne | Acne to the face | Spots cleared up within about 8 weeks of starting treatment |

The inventors also conducted a case study of a female of approximately 25 years of age who has suffered from the following conditions:

Psoriasis

The subject suffered from sporadic psoriasis around hairline, ears and eyebrows.

After utilising the soap of the present invention, the subject noticed that the areas affected by the condition were less inflamed and sore. After using the soap a second time there was a reduction in inflamed skin.

After approximately 4 days of using the soap, the sore patches cleared up.

Any re-occurrences of the symptoms associated with the condition were quickly relieved utilising the soap. The subject also observed that even when washing her face with the soap of the present invention, her skin stayed soft and remained so without irritation.

Eczema

The subject also suffered from sporadic eczema between her fingers.

At the first sign of itching, the subject utilised the soap on the affected areas. The redness and itchiness associated with her condition was alleviated almost immediately. After using the soap of the present invention 3 times in one day, the eczema had almost cleared up completely. On the second day of starting her treatment, all symptoms had diminished.

Chronic Allergic Reactions

The subject suffered from a plethora of skin reactions brought about by certain allergens.

Allergen 1

The sap of daffodils had left the subject's skin covered in a red, itchy and inflamed rash. After a week of severe discomfort, the subject utilised the soap. The symptoms associated with this condition were alleviated almost immediately after one application of the soap. After 3 days of continuing with the use of the soap, the rash had completely disappeared.

Allergen 2

The subject suffered an allergic reaction from stick sap. The sap produced a burning reaction of the skin. As soon as the subject began to feel the symptoms of an allergic reaction, the subject immediately washed the affected area thoroughly with the soap of the present invention. This stopped the reaction completely and soothed any inflammation that had started to develop. Previously, it had taken the subject between a week and a fortnight to recover from such an exposure to plant sap.

Allergen 3

The subject also reacts to exposure to sun. Usually, the exposure results in raised lumps and blotches. Could be said to resemble hives. By utilising the soap of the present invention, the subject noticed that the symptoms associated with exposure to the sun, namely, the raised lumps and blotches which prickled, were alleviated.

From the above it was observed that in all cases a marked improvement was exhibited shortly after starting treatment with the soap of the present invention.

The features disclosed in the foregoing description, or the following claims, or the accompanying drawings, expressed in their specific forms or in terms of a means for performing the disclosed function, or a method or process for attaining the disclosed result, as appropriate, may separately, or in any combination of such features, be utilised for realising the invention in diverse forms thereof.

In the present specification "comprises" means "includes or consists of" and "comprising" means "including or consisting of".

The invention claimed is:

1. A soap comprising glycerine and dried sapropel, wherein in the soap is a solid soap.

2. The soap of claim 1, wherein the soap is a sodium soap.

3. The soap of claim 1, wherein the soap is a potassium soap.

4. The soap of claim 1, wherein the sapropel is white sapropel.

5. The soap of claim 1, wherein the sapropel is black sapropel.

6. A process for making soap, the process including the steps of adding dried sapropel to the reactants and not removing the resultant glycerine from the end product or adding glycerine to the end product, wherein the soap is a solid soap.

7. A method for treating a skin disease or condition comprising applying the soap of claim 1 to affected areas of skin in an effective amount to alleviated one or more symptoms of the skin disease or condition.

8. The method of claim 7 wherein the skin disease or condition is selected from the group consisting of acne, eczema, dermatitis, psoriasis, athlete's foot and skin allergies.

* * * * *